(12) United States Patent
Scheuering et al.

(10) Patent No.: US 8,023,711 B2
(45) Date of Patent: Sep. 20, 2011

(54) METHOD FOR VESSEL ENHANCEMENT AND SEGMENTATION IN 3-D VOLUME DATA

(75) Inventors: Michael Scheuering, Nuremberg (DE); Michael Sühling, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1026 days.

(21) Appl. No.: 11/905,255

(22) Filed: Sep. 28, 2007

(65) Prior Publication Data
US 2008/0080757 A1    Apr. 3, 2008

(30) Foreign Application Priority Data

Sep. 29, 2006 (DE) .................. 10 2006 046 285
Apr. 25, 2007 (DE) .................. 10 2007 019 582

(51) Int. Cl.
*G06K 9/00* (2006.01)

(52) U.S. Cl. .................. 382/131; 382/128; 382/173

(58) Field of Classification Search .......... 382/128–132, 382/173–180
See application file for complete search history.

(56) References Cited

U.S. PATENT DOCUMENTS

| | | | |
|---|---|---|---|
| 4,945,478 A * | 7/1990 | Merickel et al. | 382/131 |
| 5,187,658 A * | 2/1993 | Cline et al. | 382/128 |
| 6,246,784 B1 * | 6/2001 | Summers et al. | 382/128 |
| 6,345,112 B1 * | 2/2002 | Summers et al. | 382/128 |
| 6,501,848 B1 * | 12/2002 | Carroll et al. | 382/128 |
| 6,556,696 B1 * | 4/2003 | Summers et al. | 382/128 |
| 6,728,566 B1 * | 4/2004 | Subramanyan et al. | 600/407 |
| 6,947,040 B2 * | 9/2005 | Tek et al. | 345/420 |
| 7,020,314 B1 * | 3/2006 | Suri et al. | 382/130 |
| 7,024,027 B1 * | 4/2006 | Suri et al. | 382/130 |
| 7,418,151 B2 * | 8/2008 | Ghosh et al. | 382/261 |
| 7,480,401 B2 * | 1/2009 | Shen et al. | 382/131 |
| 7,483,555 B2 * | 1/2009 | Ghosh et al. | 382/128 |

(Continued)

FOREIGN PATENT DOCUMENTS
DE    102004043694 A1    3/2006

OTHER PUBLICATIONS
W.J.Niessen et al., "Model-Based Segmentation of Cardiac and Vascular Images", IEEE Int. Symposium on Biomedical Imaging 2002, Proceedings, Jul. 7-10, 2002, 22-25; Others; 2002.

(Continued)

*Primary Examiner* — Manav Seth
(74) *Attorney, Agent, or Firm* — Harness, Dickey & Pierce, P.L.C.

(57) ABSTRACT

A method is disclosed for the segmented representation of vessel-like structures of an object under examination, on the basis of tomographic data, wherein a three-dimensional tomographic volume data record of the object under examination is generated and a segmentation is carried out which enhances the vessel-like structures in the representation of the tomographic data. According to an embodiment of the invention, for each voxel, the probability with which the voxel is located in a vessel structure is determined from the environmental data of the voxel with the aid of a vessel-specific filter of a spatial dimension which corresponds to the tomographic volume data record, on the basis of Gaussian functions, and these determined probabilities are additionally used as criterion for the presence of a vessel in the segmentation process for the representation of vessel structures. An embodiment of the invention also relates to a tomography system, with a device for scanning an object under examination, preferably a patient, and at least one computer system for editing tomographic image data records containing a memory for storing program code and a processor system for executing the programs, wherein program code is stored which executes the method steps of an embodiment of the method.

16 Claims, 4 Drawing Sheets

U.S. PATENT DOCUMENTS 7,839,403 B2 * 11/2010 Heigl et al. ................... 345/423
2006/0056694 A1 3/2006 Rinck et al.

OTHER PUBLICATIONS

German Office Action dated Mar. 13, 2009.
Frangi et al.: Multiscale Vessel Enhancement Filtering Image Sciences Institute MICCAI'98, vol. 1496 of LNCS p. 130-137.
Freeman et al.: The Design and Use of Steerable Filters IEEE Transactions on Pattern Analysis and Machine Intelligence 13(9), 1991 p. 891-906.
Jacob et al.: Design of Steerable Filters for Feature Detection Using Canny-Like Criteria IEEE Transactions on Pattern Analysis and Machine Intelligence vol. 26., No. 8, Aug. 2004 p. 1007-1019.

* cited by examiner $g_{xx}$  $g_{xy}$  $g_{xz}$  $g_{yy}$  $g_{yz}$  $g_{zz}$

METHOD FOR VESSEL ENHANCEMENT AND SEGMENTATION IN 3-D VOLUME DATA

PRIORITY STATEMENT

The present application hereby claims priority under 35 U.S.C. §119 on German patent application numbers DE 10 2006 046 285.8 filed Sep. 29, 2006, and DE 10 2007 019 582.8 filed Apr. 25, 2007, the entire contents of each of which is hereby incorporated herein by reference.

FIELD

Embodiments of the invention generally relate to a method for the segmented representation of vessel-like structures of an object under examination, preferably of blood vessels in a patient, on the basis of tomographic volume data. For example, at least one embodiment may relate to a method wherein a three-dimensional set of tomographic data of an object under examination having vessel-like internal structures is generated and these tomographic data are used for carrying out a segmentation which enhances the vessel-like structures in the representation.

BACKGROUND

Segmentation and analysis of blood vessels for medical imaging processes is generally known. It helps in the diagnosis and representation of vessel illnesses, OP preparation or blood flow simulations. For this purpose, imaging methods from nuclear magnetic resonance imaging and computed tomography are used which provide for a two- or three-dimensional noninvasive angiography of the vessel system.

In these angiographic methods, the vessels are in most cases additionally rendered particularly easily visible by the injection of suitable contrast agents into the circulatory system of the patient. The coronary arteries are of particular interest in this context. Their segmentation and enhancement from contrast-producing CT or MR data is decisive for determining the degree of a vessel stenosis due to soft or calcified plaques, which represents the main reason for a cardiac infarction.

In the prior art, a number of methods for vessel segmentation from two- or three-dimensional medical imaging has been proposed. Typical methods with threshold value formation or so-called "region growing" are mathematically efficient but rely completely on the measured intensity values of the image voxels. As soon as there is no further information about the geometry, these methods suffer from faulty segmentation of other contrasted regions such as the heart ventricles, bones or the aorta.

More highly developed methods are based on deformable models. However, geometric models such as generalized cylinders are normally not sufficient for being able to adequately represent complex tree structures.

Although statistical methods with preformed models are able to represent complex structures, they need prior intensive training of a large representative database. Abnormal vessel branching which, as a rule, represents the most critical places in the segmentation algorithm are frequently wrongly segmented here. Furthermore, although model-based methods are more robust against noise in the image data, many of them cannot be implemented three-dimensionally since the mathematical and operating effort increases to an extreme extent.

SUMMARY

In at least one embodiment of the invention, a simple and efficient segmenting method is disclosed which, on the one hand, can be applied to three-dimensional data with supportable effort and, on the other hand, provides sufficiently reliable output data.

The inventors have recognized that an effective and mathematically efficient segmentation of vessel structures can be achieved by a combination of threshold value considerations, known per se, on the tomographic data records, on the one hand, and the calculation of probabilities of the actual presence of vessels by filtering the tomographic data records with direction-optimized filters which approximate a vessel contour, on the other hand.

For this purpose, three-dimensional Gaussian filters can be used, for example, the familiar standard deviation σ of the Gaussian function depending on the diameter of the vessels sought. In this process, the tomographic data records are thus searched for similar structures in a mathematically efficient manner by way of such vessel-specific filters. In this context it is to be noted that the direction-oriented filters are also improved or even optimized in each case in their alignment in order to obtain reliable information about the probability of whether the voxel considered in each case is attributable to a vessel or not. To meet this requirement without setting too high a demand on the necessary computing capacity, the inventors additionally propose that when the vessel-specific filter is used which is built up of a linear combination of a number of basic filters, only the orientation of one of the basic filters is improved or even optimized by which the orientation of the remaining basic filters is fixed.

Such vessel-specific filters can be applied to the tomographic data records for a number of vessel diameters, in each case producing a probability data record. These data records can be combined before the segmentation method, wherein the maximum probability preferably can be transferred to a combined data record in each case per voxel. In the segmentation of the tomographic data records, both the intensity values and the probability values are utilized as criterion for deciding about the presence of a vessel.

In accordance with this basic finding and the subsequent detailed representation of at least one embodiment of the invention, the inventors propose the improvement of a method for the segmented representation of vessel-like structures of an object under examination, preferably of blood vessels in a patient, on the basis of tomographic data in which a three-dimensional tomographic volume data record of an object under examination with vessel-like internal structures is generated, and using this tomographic volume data record, a segmentation is carried out which enhances the vessel-like structures in the representation of the tomographic volume data record. According to at least one embodiment of the invention, this method is supplemented to the extent that for each voxel of the tomographic volume data record, the probability with which the voxel is located in a vessel structure is determined from the environmental data of each voxel with the aid of a vessel-specific three-dimensional filter h(r) on the basis of Gaussian functions, and these determined probabilities are additionally used as criterion for the presence of a vessel in the segmentation process for the representation of vessel structures.

Thus, there are now two criteria available which are largely independent of one another—absolute value or gray-scale value or value range of the tomographic recording and probability information for the presence of a vessel at the voxel considered—which can be used equivalently or also with different weighting in the segmentation.

For example, it is proposed that a linear combination of partial second-order derivations of a three-dimensional Gaussian function g(r) along the Cartesian coordinate axes x, y and z is used as filter h(r). In this arrangement, the filter can be described by the formula $$h(r)=\alpha_1 g_{xx}(r)+\alpha_2 g_{xy}(r)+\alpha_3 g_{xz}(r)+\alpha_4 g_{yy}(r)+\alpha_5 g_{yz}(r)+\alpha_6 g_{zz}(r)$$

where $\alpha_k$ represents the linear coefficients and $g_{ij}$ represents the partial second-order derivations of the spatial directions x, y, z.

In at least one embodiment of this method, the optimum orientation of the filter (h(r)) used can be determined exclusively by optimized spatial alignment of the part-filter ($g_{xx}$) from the partial second-order derivation of the three-dimensional Gaussian function along the Cartesian x coordinate in the determination of the probability that each voxel of the tomographic data record lies within a vessel.

In principle, it is advantageous if the determination of the probability that each voxel of the tomographic data record lies within a vessel is carried out several times for vessels of different diameter, the vessel diameter being determined by the standard deviation σ of the Gaussian function used. However, there is also the possibility, if only certain vessel sizes are to be considered, to select these specifically by using a filter for a particular vessel diameter or a particular range of diameters, and suppress the ultimate segmentation of other diameters by this method/device.

In principle, the part-method of the probability determination is possible with all known segmentation methods and of advantage. However, the combination with a segmentation in which vessels, per voxel, must exceed a threshold value with respect to the tomographically determined image data and a threshold value with respect to the probability values determined in order to consider the relevant voxel as belonging to a vessel, is preferably proposed.

In at least one embodiment, the preferred variant lies in that a combination of a "region growing" method and a threshold value decision on the basis of the probability values determined is utilized for the segmentation of the vessels, wherein the relevant voxel is considered as belonging to a vessel only if this situation is determined by both methods.

The method described in at least one embodiment of this document can be applied to computed tomographic, preferably medical, data records. Typical examples are the angiography of the heart, of the brain vessels or other regions and organs with a vessel structure. It must be pointed out that the tomographic data used for this purpose are obtained by using contrast agents in the body but this is not a basic prerequisite.

Apart from using X-ray computed tomography, tomographic data records from a nuclear magnetic resonance system, preferably of a patient, can also be used for utilizing the method according to the invention described in this document.

The scope of at least one embodiment of the invention also includes a tomography system, preferably for use in medicine, with a means for scanning an object under examination, preferably a patient, and at least one computer system for editing tomographic image data records containing a memory for storing program code and a processor system for executing the programs, wherein program code is stored which, in operation, executes the method steps of the method according to at least one embodiment of the invention.

BRIEF DESCRIPTION OF THE DRAWINGS

In the text which follows, embodiments of the invention, particularly the derivation of a preferred filter, is described in greater detail with the aid of the figures, only the features necessary for understanding the embodiments of invention being shown and the following reference symbols being used: 1: CT system; 2: first X-ray tube; 3: first detector; 4: second X-ray tube; 5: second detector; 6: gantry housing; 7: patient; 8: patient table; 9: system axis; 10: control and computing unit; 11: memory; 12: contrast agent pump; 13: ECG line; 14: control and data line; 15: control line; $Prg_1$-$Prg_n$ computer programs.

In detail.

DETAILED DESCRIPTION OF THE EXAMPLE EMBODIMENTS

Figure 1:
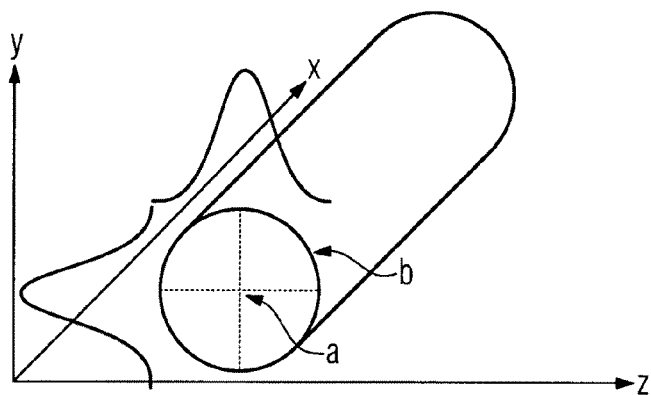
FIG. 1 shows a 3-D representation of an ideal vessel with functional representation of the image values corresponding to two Gaussian distribution curves.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

A basic concept of an embodiment of the invention lies in examining tomographic volume image data voxel by voxel with the aid of filter operations to find out the probability with which voxels considered in each case are part of a vessel structure. As a result of such an examination, a probability is to be specified with which the voxel considered in each case can be attributed to a vessel structure. For this purpose, filters can be used which reproduce a vessel cross section, that is to say when they are applied to a largely similar vessel contour in the tomographic representation generate a positive feedback and in the case of all other structures provide little to no positive feedback.

FIG. 1 shows a 3-D representation of an ideal vessel which on the outside has a uniformly low image value a which increases towards the center of the vessel in accordance with the intensity curves, shown above and on the left of the vessel, corresponding to a Gaussian distribution, up to a maximum image value b. The function corresponds to the function of the equation (3) shown further below.

Thus, for example, a Gaussian window function by which the partial second-order derivations are generated in the main Cartesian directions is suitable for spatial tomography data. The Gaussian function is:

$$g(x, y, z) = e^{-\frac{x^2+y^2+z^2}{2\sigma^2}} \quad (1a)$$

The window size can be adapted to the vessel proportions by choosing a suitable standard deviation. This method is preferred because the intensity normally scarcely varies along the vessel whereas the intensity profiles of the cross section typically have their maximum in the vessel center and rapidly decrease towards the vessel walls. In practice, filtering of the tomographic data takes place by means of a convolution with six basic filters $g_{xx}$, $g_{xy}$, $g_{xz}$, $g_{yy}$, $g_{yz}$, and $g_{zz}$, which are produced from the second partial derivation of the Gaussian function $g(x, y, z)$. For each voxel, the convolution results can be combined in a symmetric 3×3 matrix, the so-called Hesse matrix H.

$$H = \begin{pmatrix} g_{xx}*f & g_{xy}*f & g_{xz}*f \\ g_{xy}*f & g_{yy}*f & g_{xz}*f \\ g_{xz}*f & g_{yz}*f & g_{zz}*f \end{pmatrix} \quad (1b)$$

Since H is symmetric, it has real eigenvalues and can be separated into $$H=V\Lambda V^T, \quad (1c)$$

where $\Lambda=\text{diag}(\lambda_1, \lambda_2, \lambda_3)$ is the diagonal matrix of the eigenvalues and the orthogonal matrix $V=(u; v; w)$ is separated into the dependent eigenvectors u, v and w. Splitting up the eigenvalues corresponds to an orthogonal transformation of the original system of coordinates spanned by the unit vectors $e_1=(1,0,0)^T$, $e_2=(0,1,0)^T$, $e_3=(0,0,1)^T$, into a new system of coordinates which is spanned by the vectors $u=Ve_1$, $v=Ve_2$ and $w=Ve_3$.

Because the intensity does not vary very much along the vessel, an eigenvalue, for example, $\lambda_1$, is close to zero, for example $\lambda_1 \approx 0$. The fact that the vessel intensity drops significantly with increasing distance from the center axis means that two eigenvalues are negative, for example, $\lambda_2, \lambda_3 \ll 0$. Using the three eigenvalues, a measure of the probability that the local image content considered represents a vessel-like structure can be calculated. The measure of the probability presented, for example, in the printed document A. Frangi, W. Niessen, K. Vincken and M. Viergever, "Multiscale vessel enhancement filtering", W. Wells, A. Colchester and S. Delp, editors, MICCAI'98, volume 1496 of LNCS, pages 130-137, Springer-Verlag, Germany 1998, the entire contents of which are hereby incorporated herein by reference, is dependent on three free parameters which do not have any direct physical or geometric significance and the choice of which mainly influences the resultant probability. Their values and the mutual dependence must be determined by trial and error from a large quantity of data. Experiments also show that this method reacts very sensitively to noise in the image data.

In many image-processing methods, it must be possible to orient a filter variably. With a simple consideration, this can be achieved by calculating a filter mask for each desired orientation, then calculating their convolution and applying it to the image. Since the calculation of convolutions is mathematically complex, particularly in 3-D, this method is extremely complex if a large number of orientations are to be analyzed. A mathematical system can be introduced for synthesizing a filter h as linear combination of N basic filters $h_n$. The system allows the filtering result in any orientation to be calculated analytically as a function of the orientation of the basic filtering results.

$$f*h(Rr) = \sum_{n=1}^{N} c_n(R)(f*h_n)(r).$$

The 3×3 matrix R marks a three-dimensional matrix of rotation which specifies the direction in which the filter is steered. The coefficients $c_n(R)$ must be calculated from the given orientation in order to obtain the correct filtering result. It is to be noted that the convolutions $f*h_n$ of the basic filters only need be calculated once. It must be pointed out that the proposed computing scheme is limited to a limited class of the filter h which meet certain mathematical characteristics.

The inventors propose the filter h(r) as a linear combination of partial second-order derivations of a Gaussian function g(r), with $$h(r) = \alpha_1 g_{xx}(r) + \alpha_2 g_{xy}(r) + \alpha_3 g_{xz}(r) + \alpha_4 g_{yy}(r) + \alpha_5 g_{yz}(r) + \alpha_6 g_{zz}(r)$$

where the six basic filters are given by $h_1 = g_{xx}, \ldots, h_6 = g_{zz}$.

The coefficients $\alpha_n$ are determined by maximizing the filter output signal $$S = f_0 * h = \int_{R^3} f_0(r) h(-r) dr$$

of an ideal vessel signal $f_0$, with the restriction that the norm of the filter $$N^2 = \int_{R^3} |h(r)|^2 dr = 1 \quad (2)$$

is constant.

In the case where the filter input signal is disturbed by additional Gaussian white noise, the parameter $N^2$ corresponds to the gain factor of the noise variance through the filter. The inventors represent the ideal vessel $f_0$ locally as a cylinder along the x axis by means of a radial Gaussian intensity profile having the following function:

$$f_0(r) = b + (a - b) e^{\frac{y^2 + z^2}{2\sigma^2}} \quad (3)$$

The parameter a describes the intensity in the vessel center and b describes the intensity at the vessel edge.

The standard deviation of the radially decreasing intensity is selected in such a manner that it corresponds to the standard deviation of the analysis window g. In fact, it can be shown that the filter output signal h is maximum if the standard deviation of the window g corresponds to the standard deviation of the vessel image $f_0$.

This optimization problem with side condition can be solved analytically with the mathematical method of the Lagrange multipliers. The solution is given by $$h(r) = c\sqrt{\sigma} \left( \frac{2}{3} g_{xx}(r) - g_{yy}(r) - g_{zz}(r) \right) \quad (4)$$

with $$\alpha_1 = \frac{2}{3} c\sqrt{\sigma}, \alpha_2 = 0, \alpha_3 = 0,$$

$$\alpha_4 = -c\sqrt{\sigma}, \alpha_5 = 0, \alpha_6 = -c\sqrt{\sigma},$$

where $$c = \sqrt{\frac{3}{5\pi^{\frac{3}{2}}}}$$

applies.

Figure 2:
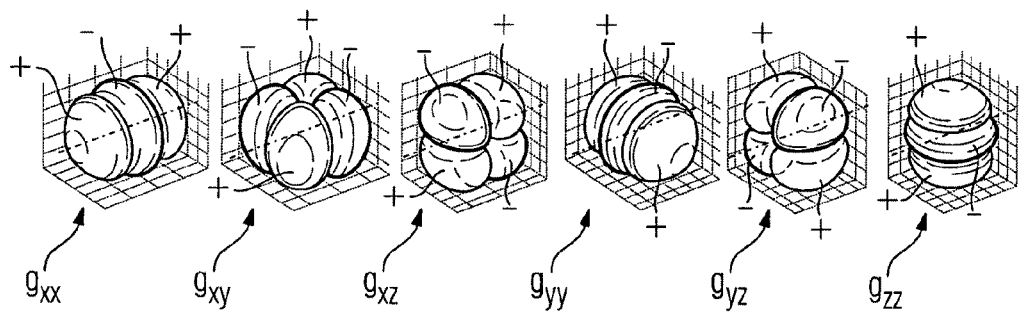
FIG. 2 shows six partial derivations $g_{xx}, \ldots, g_{zz}$ of the Gaussian function g(x, y, z) in graphic representations of Iso surfaces in the Cartesian system of coordinates.
Figure 3:
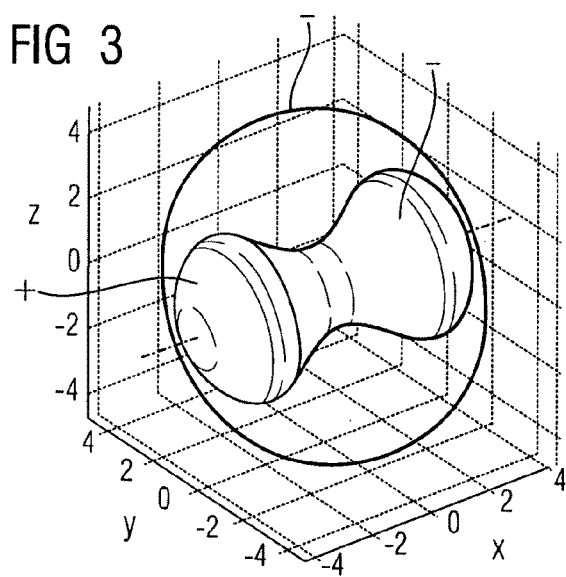
FIG. 3 shows a graphical representation of the complete filter h(r) with Iso surfaces in the Cartesian system of coordinates.

The six basic filters $g_{xx}, \ldots, g_{zz}$ and the resultant vessel filters h are shown in FIG. 2 and FIG. 3, respectively. FIG. 2 shows the six partial derivations $g_{xx}, \ldots, g_{zz}$ of the Gaussian function g(x, y, z) in graphic representations of Iso surfaces, the negative components in each case being marked by "−" and the positive components being marked by "+". FIG. 3 similarly shows the entire filter h(r). Here, too, the negative components are in each case marked by "−" and the positive components are marked by "+".

It is then necessary to find an optimum matrix of rotation R* so that the convolution of f with the rotating filter $$h^*(r) = h(R^* r)$$

becomes maximum.

The probable vessel direction is then given by the rotated x axis direction $u^* = R^* e_1$, where $e_1 = (1,0,0)^T$ designates the unit vector which represents the x axis of a Cartesian system of coordinates.

Corresponding to Euler's theorem of rotation, each 3-D rotation can be described by three parameters. In most cases, rotations are described by the following three elementary matrices of rotation:

$$R_\alpha = \begin{pmatrix} 1 & 0 & 0 \\ 0 & \cos\alpha & \sin\alpha \\ 0 & -\sin\alpha & \cos\alpha \end{pmatrix},$$

rotation around the x axis with angle $\alpha$, $$R_\beta = \begin{pmatrix} \cos\beta & 0 & -\sin\beta \\ 0 & 1 & 0 \\ \sin\beta & 0 & \cos\beta \end{pmatrix},$$

rotation around the y axis with angle $\beta$, $$R_\gamma = \begin{pmatrix} \cos\gamma & \sin\gamma & 0 \\ -\sin\gamma & \cos\gamma & 0 \\ 0 & 0 & 1 \end{pmatrix},$$

rotation around the z axis with angle $\gamma$.

Their matrix product $R_{\gamma,\beta,\alpha} = R_\gamma, R_\beta, R_\alpha$ then describes the general rotation.

The order and multiplicity of the elementary rotations can vary and is not commutative. Equation (4) easily shows that the derived filter h is radially symmetrical to the x axis. Consequently, rotation around the x axis is not required if it is applied first. The filter can be steered into any 3-D direction by carrying out two successive rotations around the y axis and around the z axis respectively, with:

$$R_{\gamma,\beta} = R_\gamma R_\beta$$

In detail, the unit vectors $e_1 = (1,0,0)^T$, $e_2 = (0,1,0)^T$, $e_3 = (0,0,1)^T$, which span the Cartesian system of coordinates, are mapped by the rotation on to:

$$u = R_{\gamma,\beta} e_1 = (\cos\gamma \cos\beta, \sin\gamma \cos\beta, -\sin\beta)^T$$

$$v = R_{\gamma,\beta} e_2 = (-\sin\gamma, \cos\gamma, 0)^T \quad (5)$$

$$w = R_{\gamma,\beta} e_3 = (\cos\gamma \sin\beta, \sin\gamma \sin\beta, \cos\beta)^T.$$

In the text which follows, it will be shown that the optimum direction $u^*$ can be determined without explicitly calculating the matrix of rotation R*. To demonstrate this, equation (4) is rewritten in the following form $$h(r) = \frac{5}{3}g_{xx}(r) - (g_{xx}(r) + g_{yy}(r) + g_{zz}(r))$$
$$= \frac{5}{3}g_{xx}(r) - \nabla^2 g(r),$$

where $\nabla^2 g(r) = g_{xx}(r) + g_{yy}(r) + g_{zz}(r)$ describes the 3-D Laplace operator.

Since the Laplace operator is isotropic, its contribution to the filter output signal is independent of the orientation of h. In consequence, the determination of the direction u*, along which h*f becomes maximum, is equivalent to determining the direction u*, along which the filter result h*f is maximum. Mathematical analyses show that the optimum vector u* is equal to the Eigen vector to the greatest eigenvalue $\lambda_{MAX}=\max(\lambda_1, \lambda_2, \lambda_3)$ of the Hesse matrix H (formula 1b). Without restricting generality, it is assumed that $\lambda_{MAX}=\lambda_1$ holds true.

The optimum filter output signal along u* is given by $$f*h^* = \frac{5}{3}\lambda_1 - (\nabla^2 g)*f = \frac{5}{3}\lambda_1 - Tr(H), \quad (6a)$$

where Tr(H) is the trace of the Hesse matrix (formula 1b). Since the trace of a quadratic matrix corresponds to the sum of the eigenvalues of this matrix, the equation (6a) can be rewritten as $$f*h^* = \frac{5}{3}\lambda_1 - Tr(H) = \frac{2}{3}\lambda_1 - \lambda_2 - \lambda_3 \quad (6b)$$

The eigenvalue separation in the three dimensional can be calculated analytically. The optimum filter orientation and its convolution result can thus be derived very efficiently without having to perform iterative estimations.

Once the optimum filter output signal of the region of interest has been calculated, it is desirable to determine a threshold value above which the local image is classified as vessel structure.

The filter output signal of the vessel model $f_0$ from equation (3) can be calculated analytically as $$f_0 * h = (a-b)\sqrt{\frac{6}{5}} \pi^{\frac{3}{4}} \sigma^{\frac{3}{2}}, \quad (7)$$

where σ is the standard deviation of the analysis window g, that is to say determines the diameter of the vessel structure sought. This makes it possible to calculate the threshold for the filter output signal simply by means of equation (7) by determining a minimum difference (a–b) between the intensity a in the vessel center and the intensity b at the vessel boundary. In the case of CT image data a preferred value for the minimum intensity difference is 100 HU. With respect to the partial volume effect in CT imaging, the minimum intensity difference for small diameters, that is to say a small σ, can be selected to be smaller than for large vessels where the local intensity medium with the vessel environment is less dominant. Suitable values can be obtained by evaluating representative CT image data records.

To avoid a false detection of very wide flat structures, for example, regions in which the cross-sectional intensity decreases rapidly in one direction but is retained in the orthogonal direction, the inventors propose to multiply the filter output signal according to formula 6b by the following isotropy factor κ

$$\kappa = 1 - \frac{||\lambda_2| - |\lambda_3||}{|\lambda_2| + |\lambda_3|} \in [0.1]. \quad (8a)$$

The factor κ approaches 0 (zero), if $|\lambda_2| \ll |\lambda_3|$ or $|\lambda_2| \gg |\lambda_3|$. This occurs, for example, if the intensity drops much more rapidly in one direction than in the orthogonal direction thereto. An isotropy factor 1, i.e. $|\lambda_2| \approx |\lambda_3|$, means that the intensity decreases uniformly with increasing radial distance from the vessel center which is the case typically for vessels. If the filter output signal according to formula 6b is combined with the isotropy factor κ, the following is obtained as vessel probability measure $$P = \kappa(f*h^*) = \left(1 - \frac{||\lambda_2| - |\lambda_3||}{|\lambda_2| + |\lambda_3|}\right)\left(\frac{2}{3}\lambda_1 - \lambda_2 - \lambda_3\right). \quad (8b)$$

Considering also the isotropy factor for the threshold value of the vessel probability measure, the inventors propose the threshold $$TV = \kappa_0(a-b)\sqrt{\frac{6}{5}} \pi^{\frac{3}{4}} \sigma^{\frac{3}{2}} \quad (9)$$

for P. $\kappa_0$ here represents the threshold of the permissible anisotropy. An advantageous choice is, e.g. $\kappa_0=0.5$.

Since the vessel filter output signal is maximum when the size of the analysis window g corresponds to the vessel thickness, the inventors propose using filters with different standard deviations $\sigma_n$ with n=1, . . . , N. For each scaling of the diameter the corresponding threshold $TV_n$ can be determined from equation (9).

The filtered data records can also be linked to an algorithm which does not determine the entire vessel but only its center line. This center line could extend along the maxima of the filter response.

According to an embodiment of the invention, this proposed vessel filter, that is to say the determination of the probability that a voxel considered can be attributed to a vessel structure (formula 6b) is combined with known segmentation processes. For this purpose the known "region growing" algorithm is preferably selected.

"Region growing" is a generally applicable algorithm which is frequently used in image segmentation and is also used in the vessel segmentation of CT image data and NMR image data. Starting from a starting point selected manually in most cases, this technique segments images by continuously adding voxels to a region already segmented if their intensity exceeds a pre-defined threshold value $T_{Min}$. As an improvement, the inventors preferably propose to add voxels only if they meet the following two criteria:

1.) the voxel intensity is greater than the minimum threshold value $T_{Min}$
and
2.) the vessel probability measure exceeds the threshold value $TV_n$ at least in a filtered data record for a particular vessel diameter or, respectively, in accordance with a particular standard deviation $\sigma_n$, corresponding to the instruction: $P_1 \geq TV_1, \ldots, OR, \ldots P_N \geq TV_N$.

To avoid unnecessary computing expenditure, the output signal of the vessel filter can also be calculated only for voxels which are considered during the "region growing" process. Although precalculation of the filter output signal of the complete image data is possible, it requires increased computing effort as long as the vessel structure only takes up a fraction of the entire volume.

To reduce the mathematical complexity even further, the vessel probability criterion can be applied, as an alternative and disregarding the abovementioned rules for 1.) and 2.), only when the purely intensity-based ""region growing"" method "runs out" into non-vessel regions. These transitional areas can be bridged by temporarily switching into the vessel analysis mode (filtering with h(r)).

Figure 4:
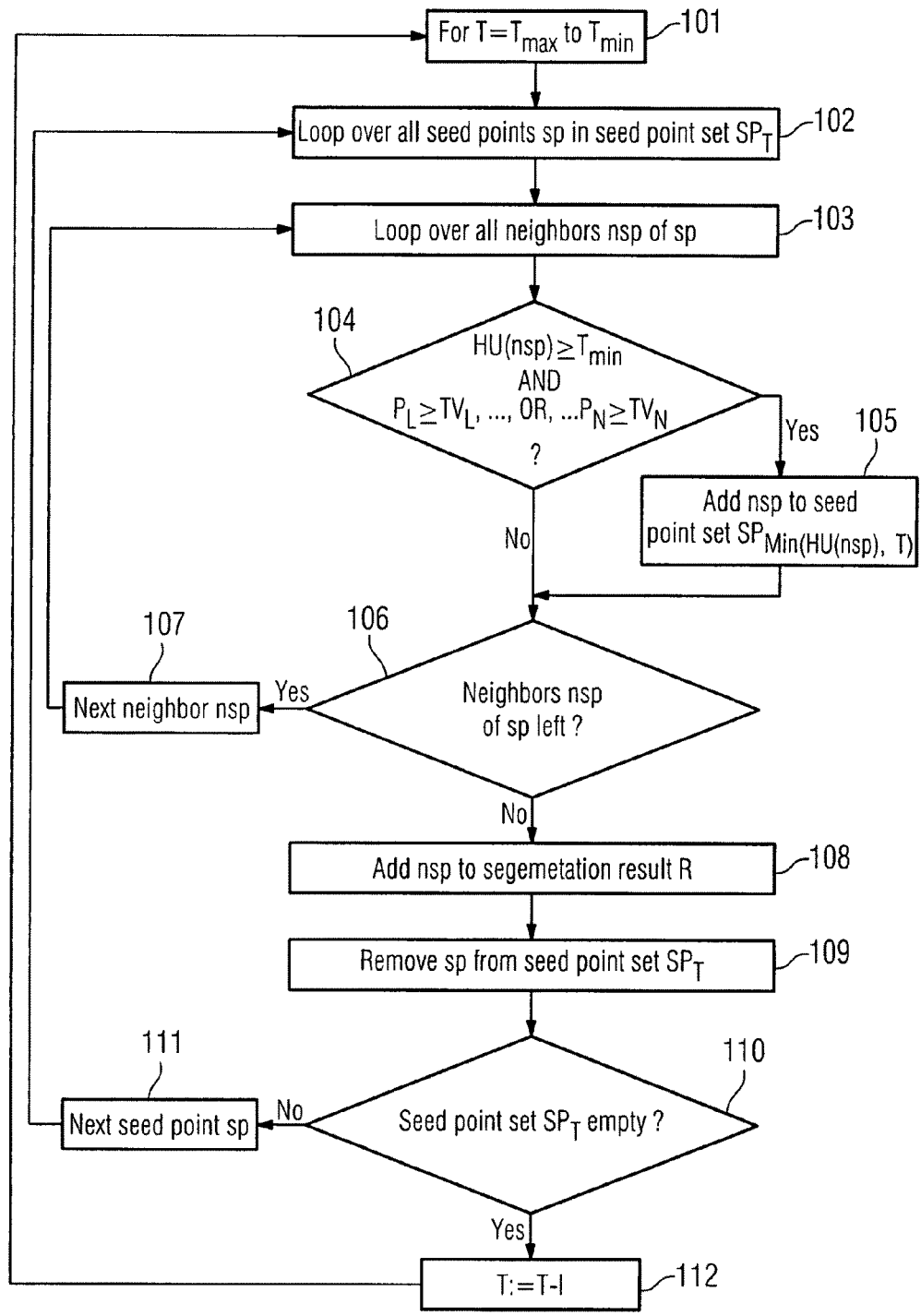
FIG. 4 shows a flowchart of a preferred segmentation method of a combination of the proposed vessel probability measure and "region growings"

FIG. 4 shows a flowchart of a method according to an embodiment of the invention with an exemplary "region growing" algorithm with the method steps 101 to 112 which utilizes both criteria of image intensity and vessel probability measure. In detail, the following method steps signify in:

101: carry out the method over the interval $[T_{min}, T_{max}]$, where T describes the gray-scale values of the voxels which are considered part of a vessel;
102: execute a loop over all seed points sp in the set of seed point voxels with one set each for each gray-scale value T;
103: execute a loop over all neighboring seed points nsp of the seed point sp;
104: in case of a yes decision, branch to method step 105 and in the case of a no decision, branch to method step 106, if—and this is the significant contribution of the invention—both conditions $(HU(nsp) \geq T_{min})$ and $(P_1 \geq TV_i, \ldots OR \ldots P_N \geq TV_N)$ are met, where HU(nsp) is the gray-scale value of the voxel nsp in HU units and $P_i$ represents the probability of a voxel being arranged within the vessel;
105: this is where this nsp is added to the set of seed points $SP_{Min(HU(nsp),T)}$;
106: decision whether there are further neighboring voxels nsp to the voxel sp, if "yes" branch to 107, if "no" branch to 108;
107: selection of the next neighboring voxel nsp and continuing the loop at 103;
108: add the voxel sp to the segmentation result R, where R is a set of voxels which contains all segmented voxels;
109: remove voxel sp from the set of seed points $SP_T$;
110: check if the set of seed points $SP_T$ is empty, if "no" branch to 112, if "yes" branch to 111;
111: select the next seed point sp and continue the loop at 102;
112: reduce the value T by 1 with T:=T−1 and continue the loop at 101.

The essential factor here is that in the decision step 104, the probability calculated according to an embodiment of the invention is also taken into consideration in the manner of a threshold value in the segmentation.

Figure 5:
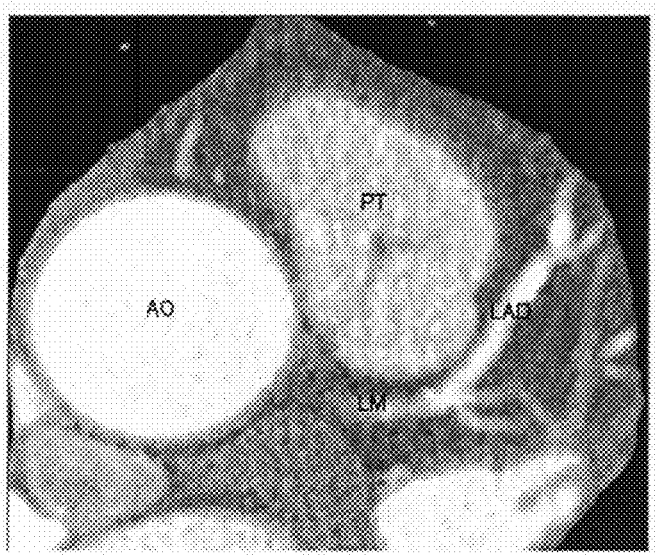
FIG. 5 shows a CT sectional image representation of a heart, recorded with contrast agent in the blood without segmentation.

For example, the filter according to an embodiment of the invention was applied to CT angiography data for segmenting coronary arteries. An axial section of an exemplary volume data record is shown in FIG. 5, where: AO=aorta, PT=pulmonary artery, LAD=left anterior descending artery, LM=left main artery.

Figure 6:
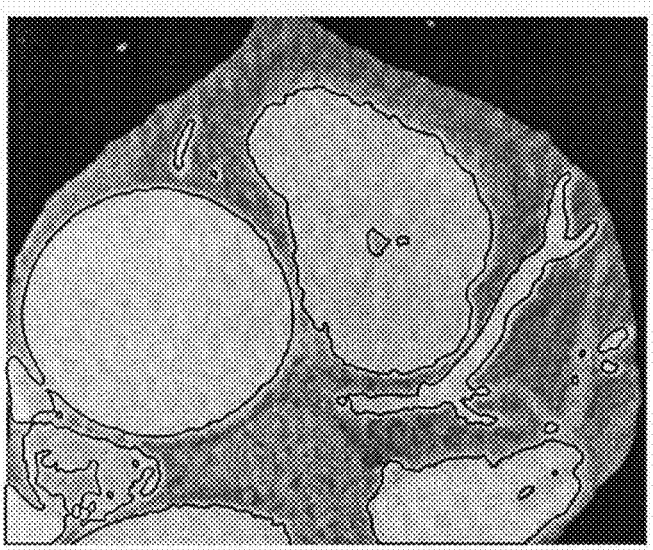
FIG. 6 shows a CT sectional image representation from FIG. 5 with segmentation only on the basis of threshold value formation of the image values.

FIG. 6 shows the segmentation by simple threshold value formation of the original input data. It results in larger false regions such as e.g. the aorta enriched with contrast agents or heart ventricles which are shown enhanced. The simple "region growing" method would immediately "run out" into these adjoining regions.

Figure 7:
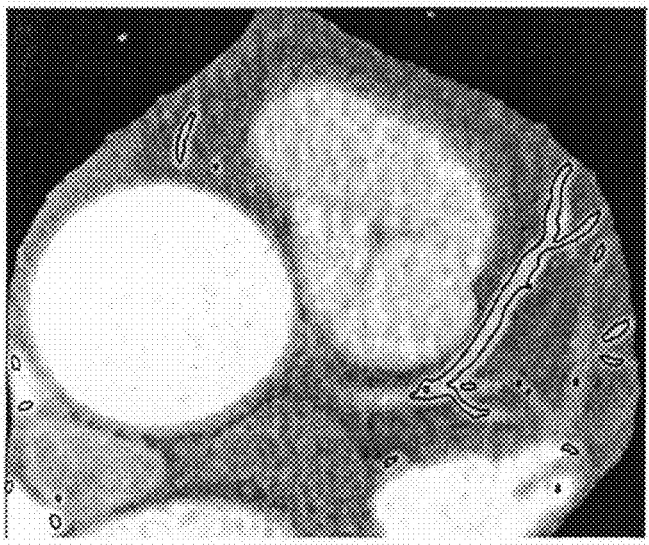
FIG. 7 shows a CT sectional image representation from FIG. 6 with segmentation edited according to an embodiment of the invention.

In contrast, the proposed vessel filter correctly identifies the desired coronary arteries as shown in FIG. 7. Segmented regions are enhanced here, too. In this process, a filter with a single simple sigma value ($\sigma$=1 mm) was used. It must be pointed out that only those vessel regions are detected which actually show a vessel structure having approximately equal, previously selected vessel diameter.

Figure 8:
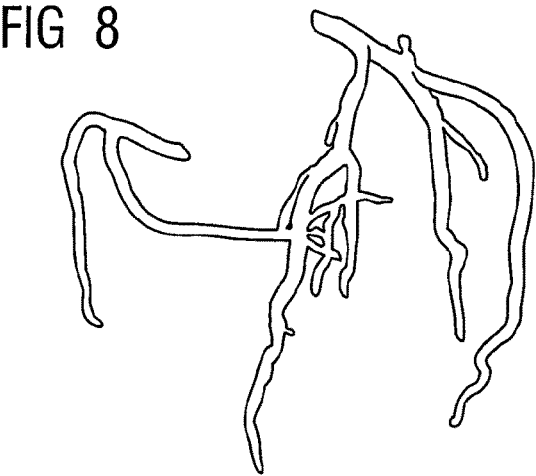
FIG. 8 shows a completely segmented CT sectional image from FIG. 5 with the method according to an embodiment of the invention.

FIG. 8 shows the final result of a complete segmentation with the "region growing" algorithm method according to an embodiment of the invention and with application of the filter h(r) to a single selected diameter. The "region growing" process was initialized by setting a seed point manually in the aorta exit at the left or right coronary artery, respectively. The coronary system is clearly segmented without leaks into the adjoining cavities. In addition, the segmentation result can be improved by filtering over a number of sigma values.

In summary, this document introduces a novel vessel filter which shows vessel-like structures three-dimensionally in an improved manner. By way of example, an embodiment of this method was integrated into a segmentation method based on "region growing" processes. The main advantages of an embodiment of reside in that:

1.) with respect to the mathematical effort, the filter is just as efficient as methods already in existence but is more robust with respect to noise in the image data records;
2.) the inventors propose an intuitive threshold for the filter output signal. This threshold reflects physical/geometric characteristics, e.g. contrast and isotropy of the vessel intensity; and
3.) the integration of the proposed vessel enhancement in "region growing" processes brings great success and a mathematically attractive vessel segmentation method without needing explicit geometric or statistical models.

It must also be pointed out that the method according to an embodiment of the invention can be performed not only in connection with CT data but also with tomographic MR data. In this case, the criterion of adaptation used is not HU values but other gray-scale values or color values of the image representation.

Figure 9:
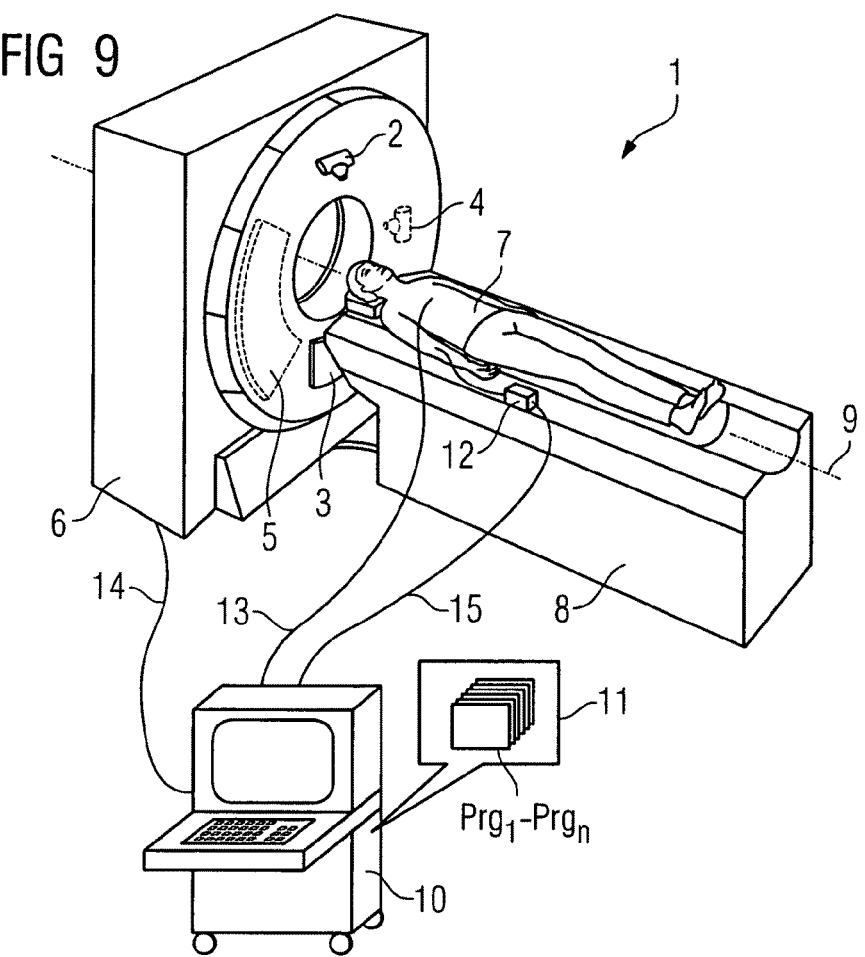
FIG. 9 shows an example imaging medical system for application of the method according to an embodiment of the invention in the form of a CT.

FIG. 9 therefore shows by way of example a CT system 1 according to an embodiment of the invention, for all known medical imaging tomographic systems such as NMR, ultrasonic, PET, SPECT and CT systems, with a gantry housing 6 in which the rotatable gantry frame is located which, however, has not been drawn explicitly here. On the patient table 8, a patient 7 to be examined is lying who can be pushed along the system axis 9 during the rotation of the gantry frame through an opening in the gantry housing which approximately describes the scanning range of the focus detector systems. By way of example, such a CT system has at least one focus detector system consisting of an X-ray tube 2 with the focus generated there and an oppositely located detector system 3 having at least one detector row, in most cases a multiplicity of detector rows arranged next to one another. Optionally, one or two further focus detector systems can be installed for improving the pick-up power and/or temporal resolution. In this representation, an optional second focus/detector system with a second X-ray tube 4 and a second detector 5 is indicated dashed.

The CT system 1 is controlled by a control and computing unit 10 via the control and data line 14, wherein the reconstruction, evaluation and the method according to an embodiment of the invention can also be run on this computing unit with the aid of the programs $Prg_1$ to $Prg_n$ stored in an internal memory 11 or on a memory medium. In addition, an optionally applicable contrast agent pump 12 with its control line 15 is shown in order to provide for the contrast agent application normally used for cardiac or general vessel recordings. It is controlled via the control and computing unit 10. In addition, an ECG line 13 from the patient 7 to the control and computing unit 10 is shown which also handles the operation of an ECG such as is necessary, for example, in most cases of cardiac recordings.

Additionally, it should also be pointed out that the scope of an embodiment of the invention is intended to contain any type of generation of the recordings, that is to say with or without contrast agent and/or with or without ECG triggering and/or with one or more focus detector systems.

However, the editing of the volume data and/or the execution of the method according to an embodiment of the invention can also be transferred to other computing stations without departing from the scope of the invention. It is also understood that the aforementioned features of an embodiment of the invention can be used not only in the combination specified in each case but also in other combinations or by themselves without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the segmented representation of vessel-like structures of an object under examination on the basis of tomographic data, comprising:

generating a three-dimensional tomographic volume data record of an object under examination having vessel-like internal structures;

carrying out, using the generated tomographic volume data record, a segmentation which enhances the vessel-like structures in the representation of the tomographic data;

determining, for each voxel of the tomographic volume data record, the probability with which the voxel is located in a vessel-like structure from environmental data of the voxel with the aid of a vessel-specific filter of a spatial dimension which corresponds to the tomographic volume data record, on a basis of Gaussian functions; and using the determined probabilities as criterion for the presence of a vessel in the segmentation process for the representation of the vessel-like structures, wherein the filter uses a linear combination of partial second-order derivations of a three-dimensional Gaussian function along a Cartesian coordinate axes, and wherein, and in the determining of the probability, an optimum orientation of the filter used is determined exclusively by optimized spatial alignment of the filter from the partial second-order derivation of the three-dimensional Gaussian function along a Cartesian x coordinate.

2. The method as claimed in claim 1, wherein the filter is determined by the following formula $$h(r)=\alpha_1 g_{xx}(r)+\alpha_2 g_{xy}(r)+\alpha_3 g_{xz}(r)+\alpha_4 g_{yy}(r)+\alpha_5 g_{yz}(r)+\alpha_6 g_{zz}(r)$$

where $\alpha_k$ describes linear coefficients and $g_y$ describes the partial second-order derivations of spatial directions x, y, z.

3. The method as claimed in claim 1, wherein, as the filter, an optimally oriented filter $h^*(r)$ is used, which is described by the following formula:

$$f * h^* = \frac{5}{3}\lambda_1 - Tr(H) = \frac{2}{3}\lambda_1 - \lambda_2 - \lambda_3,$$

where $\lambda_i$, i=1, 2, 3, are eigenvalues of a Hesse matrix H.

4. The method as claimed in claim 3, wherein the determining of the probability with which the voxel lies within the vessel-like structure is described by the following formula:

$$P=\kappa(f*h^*),$$

where a value $\kappa$ can assume values of greater than 0 up to 1.

5. The method as claimed in claim 4, wherein the value $\kappa$ is calculated with:

$$\kappa = 1 - \frac{||\lambda_2| - |\lambda_3||}{|\lambda_2| + |\lambda_3|}.$$

6. The method as claimed in claim 1, wherein the determination of the probability that each voxel of the tomographic volume data record lies within the vessel-like structure is performed once for vessel-like structures of a particular diameter, the vessel-like structures diameter being determined by a standard deviation $\sigma$ of the Gaussian function used.

7. The method as claimed in claim 1, wherein the determination of the probability that each voxel of the tomographic volume data record lies within the vessel-like structure is carried out several times for the vessel-like structures of different diameter, the vessel-like structures diameter being determined by a standard deviation $\sigma$ of the Gaussian function used.

8. The method as claimed in claim 1, wherein, for the segmentation of the vessel-like structures, a first threshold value with respect to the tomographically determined image data and a second threshold value of the determined probability values is utilized per voxel and a relevant voxel is considered as belonging to the vessel-like structure only when both the first threshold value and the second threshold value are exceeded.

9. The method as claimed in claim 8, wherein the first threshold value is calculated with:

$$TV = \kappa_0(a-b)\sqrt{\frac{6}{5}\pi^{\frac{3}{4}}\sigma^{\frac{3}{2}}}$$

where:
  a is a signal intensity in a vessel center;
  b is a signal intensity at a vessel boundary;
  $\kappa_0$ is a fixed threshold value in an interval, which takes into consideration an anisotropy of the vessel-like structure.

10. The method as claimed in claim 1, wherein a combination of a region growing method and a threshold value decision on a basis of the probability values determined is utilized for the segmentation of the vessel-like structures.

11. The method as claimed in claim 1, wherein the probability of the presence of the vessel-like structure at the voxel considered is determined only if, in a threshold value method based on voxel intensities, the voxel considered is considered as belonging to the vessel-like structure.

12. The method as claimed in claim 10, wherein a relevant voxel is considered as belonging to the vessel-like structure only if this situation is determined by both the region growing method and the threshold value decision is utilized.

13. The method as claimed in claim 1, wherein the method is applied to computed tomographic data records.

14. The method as claimed in claim 1, wherein the method is applied to tomographic volume data records from a nuclear magnetic resonance system.

15. A tomography system, comprising:
a scanner to scan an object under examination; and
at least one computer system for editing tomographic image data records, including a memory for storing program code and a processor system for executing the programs, the program code being stored which, in operation, executes:
  generating a three-dimensional tomographic volume data record of the object under examination having vessel-like internal structures;
  carrying out, using the generated tomographic volume data record, a segmentation which enhances the vessel-like structures in the representation of the tomographic data;
  determining, for each voxel of the tomographic volume data record, the probability with which the voxel is located in the vessel-like structure from environmental data of the voxel with the aid of a vessel-specific filter of a spatial dimension which corresponds to the tomographic volume data record, on a basis of Gaussian functions; and
  using the determined probabilities as criterion for a presence of the vessel-like structure in the segmentation process for the representation of the vessel-like structures, wherein the filter uses a linear combination of partial second-order derivations of a three-dimensional Gaussian function along a Cartesian coordinate axes and wherein, in the determining of the probability, an optimum orientation of the filter used is determined exclusively by optimized spatial alignment of the filter from the partial second-order derivation of the three-dimensional Gaussian function along a Cartesian x coordinate.

16. A non-transitory computer readable medium including program segments for, when executed on a computer device, causing the computer device to implement the method of claim 1.

* * * * *